United States Patent
Hirschberg et al.

[19]

[11] Patent Number: 5,814,086
[45] Date of Patent: Sep. 29, 1998

[54] PEREX RESPIRATORY SYSTEM STIMULATION UPON TACHYCARDIA DETECTION

[75] Inventors: Jakub Hirschberg, Täby; Hans Strandberg, Sundbyberg, both of Sweden

[73] Assignee: Pacesetter AB, Solna, Sweden

[21] Appl. No.: 950,138

[22] Filed: Oct. 14, 1997

[30] Foreign Application Priority Data

Oct. 18, 1996 [SE] Sweden ................................ 9603841-9

[51] Int. Cl.⁶ ....................................................... A61N 1/38
[52] U.S. Cl. .............................................. 607/14; 607/42
[58] Field of Search ............................. 607/2, 9, 14, 15, 607/20, 42

[56] References Cited

U.S. PATENT DOCUMENTS

| | | | |
|---|---|---|---|
| 4,198,963 | 4/1980 | Barlalow et al. ............................ | 607/5 |
| 4,541,417 | 9/1985 | Krikorian et al. ......................... | 600/17 |
| 5,081,987 | 1/1992 | Nigam . | |
| 5,265,604 | 11/1993 | Vince . | |

FOREIGN PATENT DOCUMENTS

WO 86/00234   1/1986   WIPO .
WO 93/0274    2/1993   WIPO .

OTHER PUBLICATIONS

Abstract 735, 736 from Cardiostim Congress, Feb., 1995 in St. Petersburg, Russia, "Modulatory Effects of the Regulatory Peptides on the Parasympathetic Regulation of the Cardiac Rhythm," Pocrovsky et al.

*Primary Examiner*—William E. Kamm
*Assistant Examiner*—George R. Evanisko
*Attorney, Agent, or Firm*—Hill & Simpson

[57] ABSTRACT

A tachycardia eliminating apparatus includes a heartbeat detector which detects heartbeats in an input heart activity signal which delivers an output heartbeat signal indicating each detected heartbeat, a tachycardia detector coupled to the output of the heartbeat detector which generates a tachycardia indication signal in response to a detected tachycardia status of a heart as reflected in the heartbeat signal, and a respiratory system stimulator coupled to the output of the tachycardia detector and generating an output respiratory system stimulation signal for stimulating a respiratory system to achieve a stimulated breathing rate, with the ratio of the detected heartbeat rate to the stimulated breathing rate corresponding to a predetermined value.

14 Claims, 4 Drawing Sheets

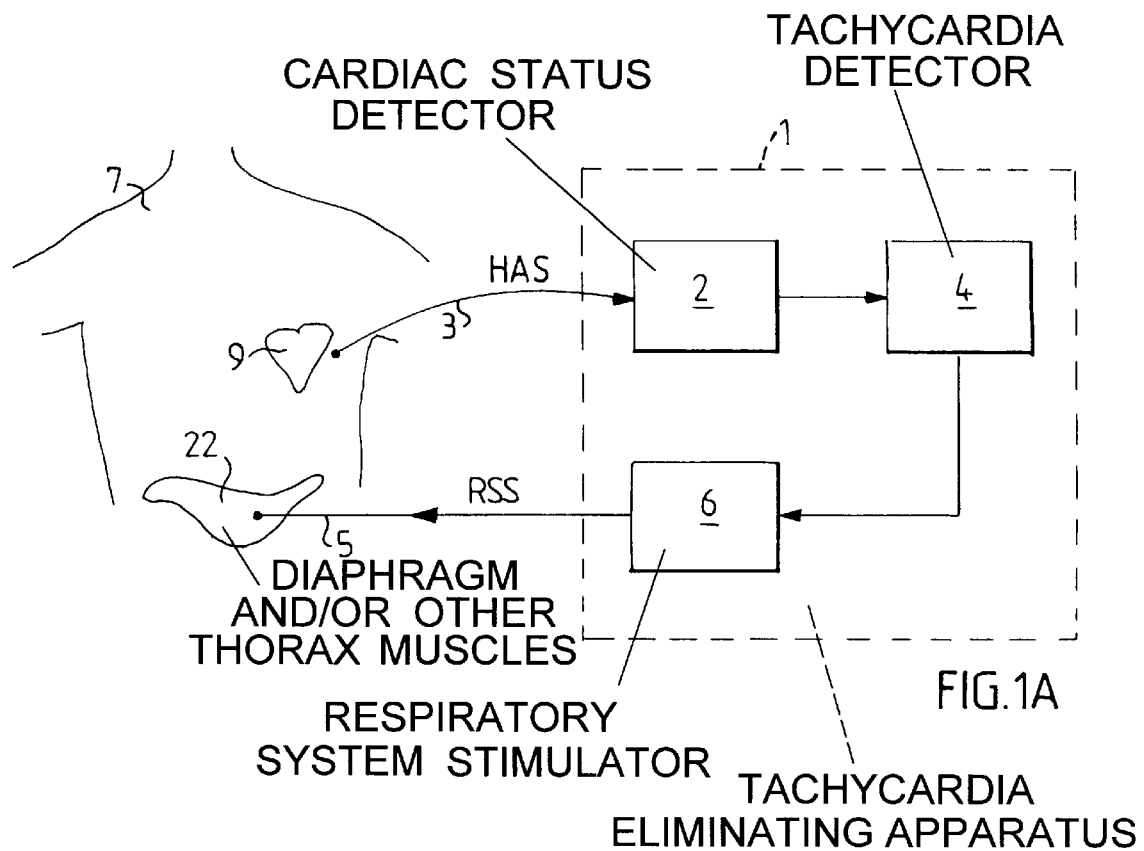
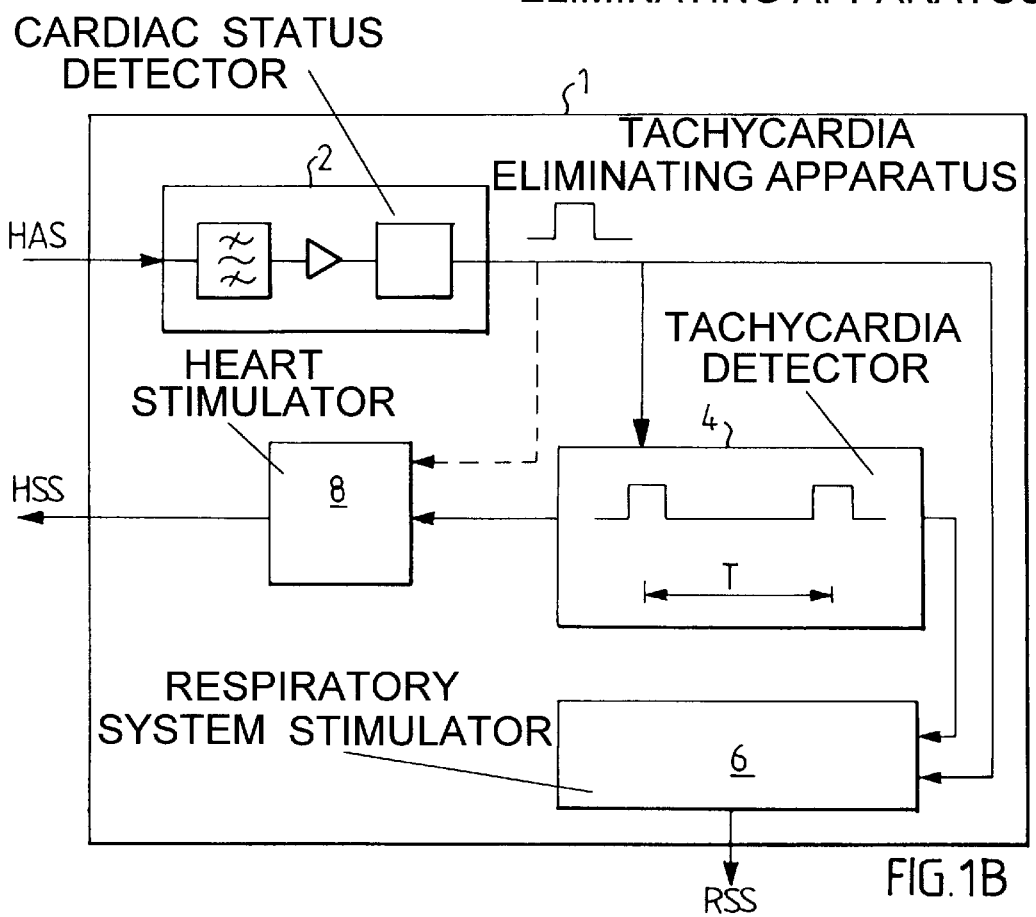

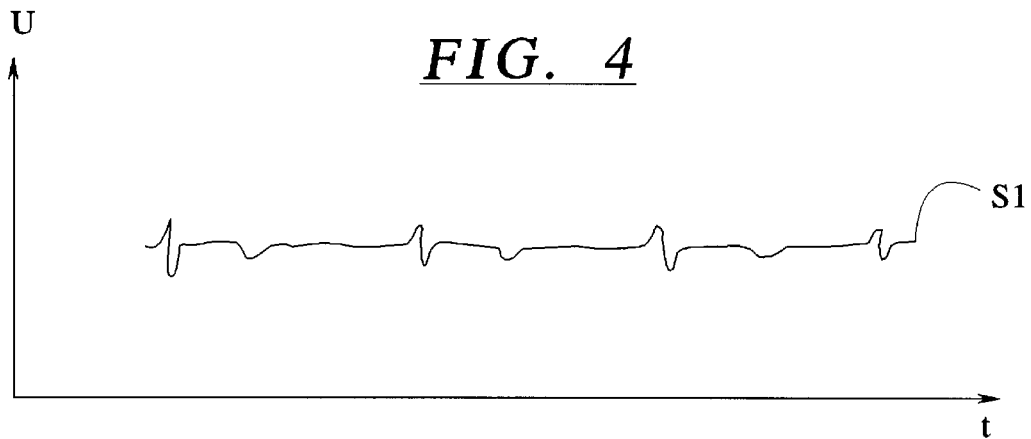
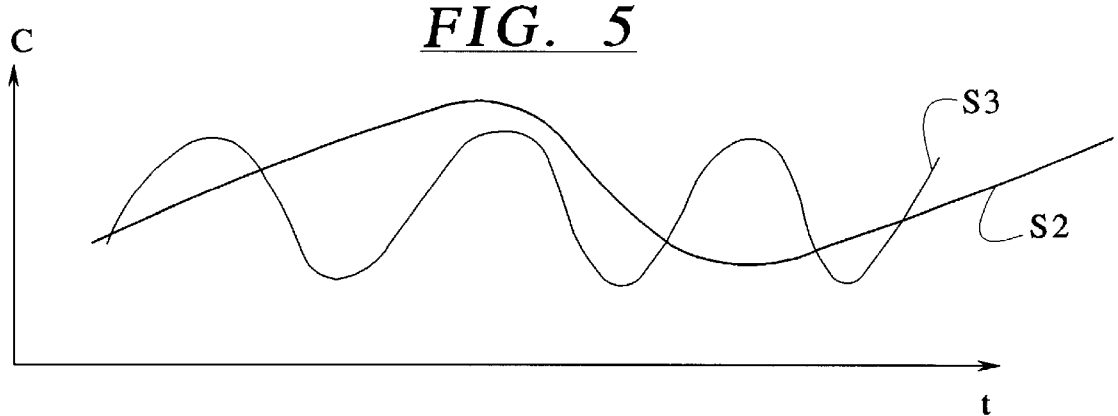
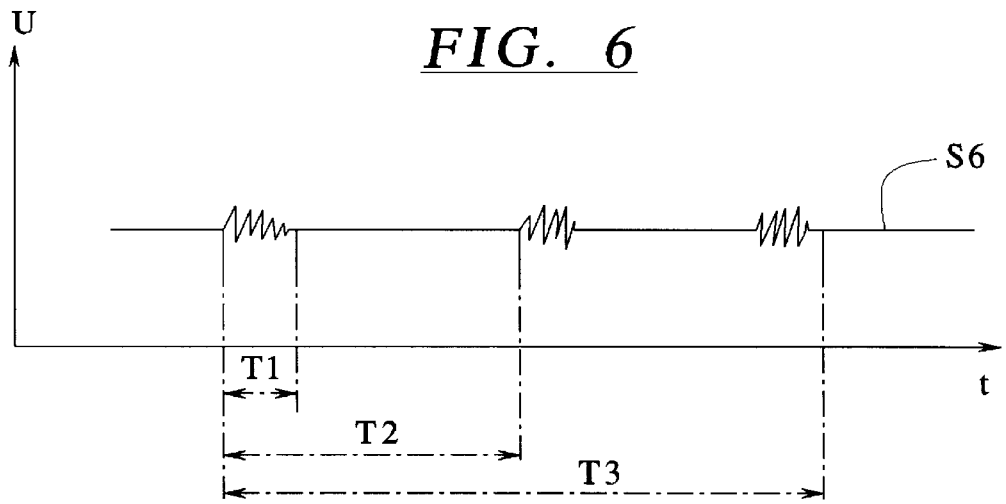
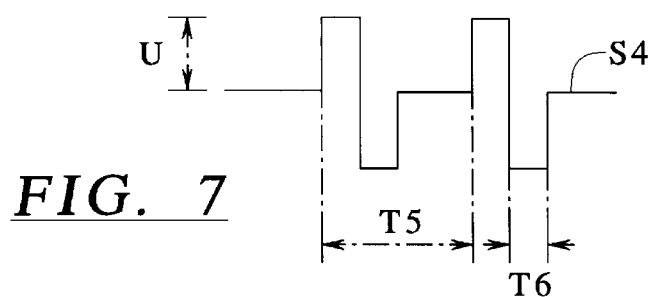

PEREX RESPIRATORY SYSTEM STIMULATION UPON TACHYCARDIA DETECTION

BACKGROUND OF THE INVENTION

1. Field of the Invention

The present invention relates to an apparatus for stimulating living tissue.

2. Description of the Prior Art

Normal rhythms of the heart are essentially regular with frequencies between 50 and 100 beats/minute depending mainly on the current body activity. Any deviation from this normal rate is called an arrhythmia, including faster or slower regular rhythms. A fast rhythm is generally called a tachycardia or a tachyarrhythmia, and a slow rhythm is called a bradycardia or a bradyarrhythmia.

The rhythm of the heart is normally initiated in the sinus node, but there is a possibility of spontaneous activity arising in different foci of the entire cardiac conduction system, i.e. the atriums, AV-node, His bundle, right and left bundle branches and Purkinje system. The reason why the sinus node normally controls the contraction of the heart is that this is the focus with the highest natural frequency, i.e. with a normal discharge frequency in the range of 50–100 pulses/minute. The natural frequency of electrically pulsing foci outside the sinus node, also referred to as ectopic foci, decreases with increasing distance from the sinus node. For example, the natural frequency of the atriums is normally 45–50 pulses/minute, of the AV-node 40–45 pulses/minute and of the ventricular structures <35 pulses/minute.

The frequencies of ectopic foci, however, may change for different reasons and interfere with the normal sinus rhythm, thereby causing ectopic rhythms or beats of the heart. Ectopic beats may in turn initiate a more serious arrhythmia, such as a re-entry tachycardia, atrial or ventricular fibrillation and atrial or ventricular flutter. It is therefore an important task in cardiac pacing and defibrillation technology to detect and eliminate ectopic beats.

It is widely known to control the rhythm of the heart by means of a pacemaker, such as the one described in, for example, European Application 0 387 363. It is also known to correct a disturbed heart rhythm by means of a defibrillator. In apparatuses of this kind the current rhythm of the heart is sensed, and when needed stimulation signals are transferred to the heart muscle via a stimulation electrode in order to achieve a desired rhythm.

It is also known that there is a mutual influence between breathing and cardiac rhythms. This was discussed at the Cardiostim Congress 1995 in St. Petersburg, Russia, where Professor W. M. Pokrowski presented experimental studies that showed how fast breathing rate synchronized with heart rate could reduce or eliminate a tachycardia. In particular, previously frequent ectopic extra beats were avoided with this method.

A method and an apparatus for diaphragmic stimulation for the purpose of effecting respiration in order to maintain an adequate concentration of oxygen in the blood of a human being are known, for example, from PCT Application WO 86/00234.

Known apparatuses for correcting heart arrhythmias are in principle devised to generate and deliver an electric shock to the heart muscle in order to force the heart out of a pathological rhythm. Such shocks can be quite brutal and the whole cardiac conductive system is thereby blocked for some time until a desired rhythm is induced and established. Apparatuses of this kind are primarily suitable for stopping tachycardias.

Tachycardia of different kinds are, however, not so easily treated, and in particular it has become apparent that known apparatuses are not really adequate for preventing entry into a pathological heart rhythm in response to detected tendencies or early signs of a tachycardia. Therefore, there is a need for an apparatus with the capability of providing a more gentle and prophylactic heart stimulation.

SUMMARY OF THE INVENTION

An object of the present invention is to provide an apparatus for eliminating a detected established (i.e., already occurring) tachycardia.

A further object of the present invention is to provide an apparatus which detects impending tachycardia and which takes steps then to eliminate the occurrence of tachycardia.

These objects are achieved in an apparatus constructed in accordance with the principles of the present invention which is devised for indirect stimulation of the heart by stimulating the respiratory system, such that the stimulated breathing rate is synchronized with the detected cardiac rate in order to eliminate a detected tachycardia. The invention utilizes the anatomical fact that there is a mutual interdependence between breathing rate and heart rate. In particular it is possible to induce a predetermined desired heart rate by stimulating the respiratory system to produce a breathing rate corresponding to the desired heart rate.

An inventive apparatus for eliminating a heart tachycardia includes a cardiac status detector, e.g., in the form of a heartbeat detector, a tachycardia detector and a respiratory system stimulator. The cardiac status detector is devised to detect the status of the cardiac system by analyzing an input cardiac activity signal. In an embodiment wherein the cardiac status detector is a heartbeat detector, the heartbeat detector operates in a known manner for detecting heartbeats in an input heart activity signal, such as an ECG signal, and to deliver an output heartbeat signal indicating each detected heartbeat. The tachycardia detector is coupled to the output of the heartbeat detector and is preferably devised to detect the period between consecutive heartbeats and to deliver an output tachycardia indication signal in response to a tachycardia status detected in the heartbeat signal. This may, for example, be achieved by comparing the detected heartbeat rate with a predetermined rate or a predetermined limit value. The respiratory system stimulator is coupled to the output of the tachycardia detector and is devised to generate an output respiratory system stimulation signal suitable for stimulating a respiratory system in order to achieve a breathing rate, with the ratio of the detected heartbeat rate to the stimulated breathing rate corresponding to a predetermined value, or with the breathing rate corresponding to a predetermined desired heartbeat rate.

In an embodiment of the invention suitable for external use, i.e. placed outside a patient's body, the inventive apparatus is devised to deliver a stimulation signal suitable for controlling an arrangement for mechanical induction of a certain breathing rate. Currently it is considered that the most useful mechanical breathing arrangement is a ventilator capable of providing the lungs of a patient with air or another suitable gas or mixture of gases. An embodiment for this arrangement is preferably provided with an integrated or separate ventilator controlling unit which is able to be coupled to the output of the respiratory system stimulator. The ventilator controlling unit is further able to be coupled to a ventilator and is devised to control the ventilator in response to a respiratory system stimulating signal. An external embodiment of this kind may, for example, take the heart activity signal from a surface ECG arrangement.

In another embodiment, the inventive apparatus is also provided with a heart stimulator is devised to stimulate a heart directly in a per se known manner. The heart stimulator is coupled to an output of the tachycardia detector and/or to an output of the heartbeat detector, and generates an output heart stimulation signal, which in a known manner is delivered to the heart muscle via a heart stimulation electrode system.

In a version of this embodiment a synchronization unit synchronizes the respiratory system signals with the direct heart stimulation signals. The synchronization unit is coupled to an output of the tachycardia detector and to an input of the heart stimulator. Another input of the synchronization unit may optionally also be feed-back coupled to the output of the heart stimulator. The synchronization unit is further coupled to an input of the respiratory system stimulator. In order to synchronize the output stimulation signals, the synchronization unit triggers the heart stimulator and the respiratory system stimulator to deliver stimulation signals in response to the tachycardia indication signal such that the respiratory system stimulation signal has a predetermined time relation to the heart stimulation signal. The synchronization may, for example, be carried out with a suitable time delay.

Different organs of the respiratory system may be stimulated in order to induce breathing as long as they are capable of triggering a coordinated activity in the respiratory system. In one embodiment of the invention the respiratory system stimulator is devised to deliver a stimulation signal suitable for stimulating a respiratory system muscle, for example, the diaphragm. In another embodiment, a stimulation signal suitable for stimulating a respiratory system nerve is delivered, for example a signal for stimulating the nervus pherenicus.

A further embodiment of the invention is implantable and in this embodiment each signal input and output is able to be coupled to implantable stimulation electrodes of suitable design. This embodiment may be realized as a specialized apparatus or may be incorporated in an otherwise known implantable heart stimulator, such as a pacemaker or a defibrillator.

Further embodiments of the invention may be devised to stimulate only selected parts of the heart, e.g. an atrium, to beat in synchronization with breathing muscles by means of the inventive apparatus coupled to a specifically situated cardiac stimulation electrode and a breathing muscle or nerve stimulation electrode.

With the inventive apparatus the heart rate may be controlled in a mild manner which is suitable for preventing or eliminating pathological states of the heart in response to early signs of an impending tachycardia or an established tachycardia. A heart rhythm deviating from a normal rhythm shows an increased inclination to fall into an arrhythmia, and with the inventive apparatus it is possible to interfere at an early stage, thereby avoiding the cruder heart stimulation methods employed in known heart stimulators. Using the inventive apparatus the heart is, so to speak, massaged into adopting or maintaining a certain heart rate.

DESCRIPTION OF THE DRAWINGS

FIG. 1A shows schematically a block diagram of an embodiment of the inventive tachycardia eliminating apparatus coupled to a human body.

FIG. 1B is a block diagram showing functional components of an embodiment of the invention.

FIGS. 4–7 are diagrams showing the general form of signals involved with the inventive apparatus.

DESCRIPTION OF THE PREFERRED EMBODIMENTS

Figure 1C:
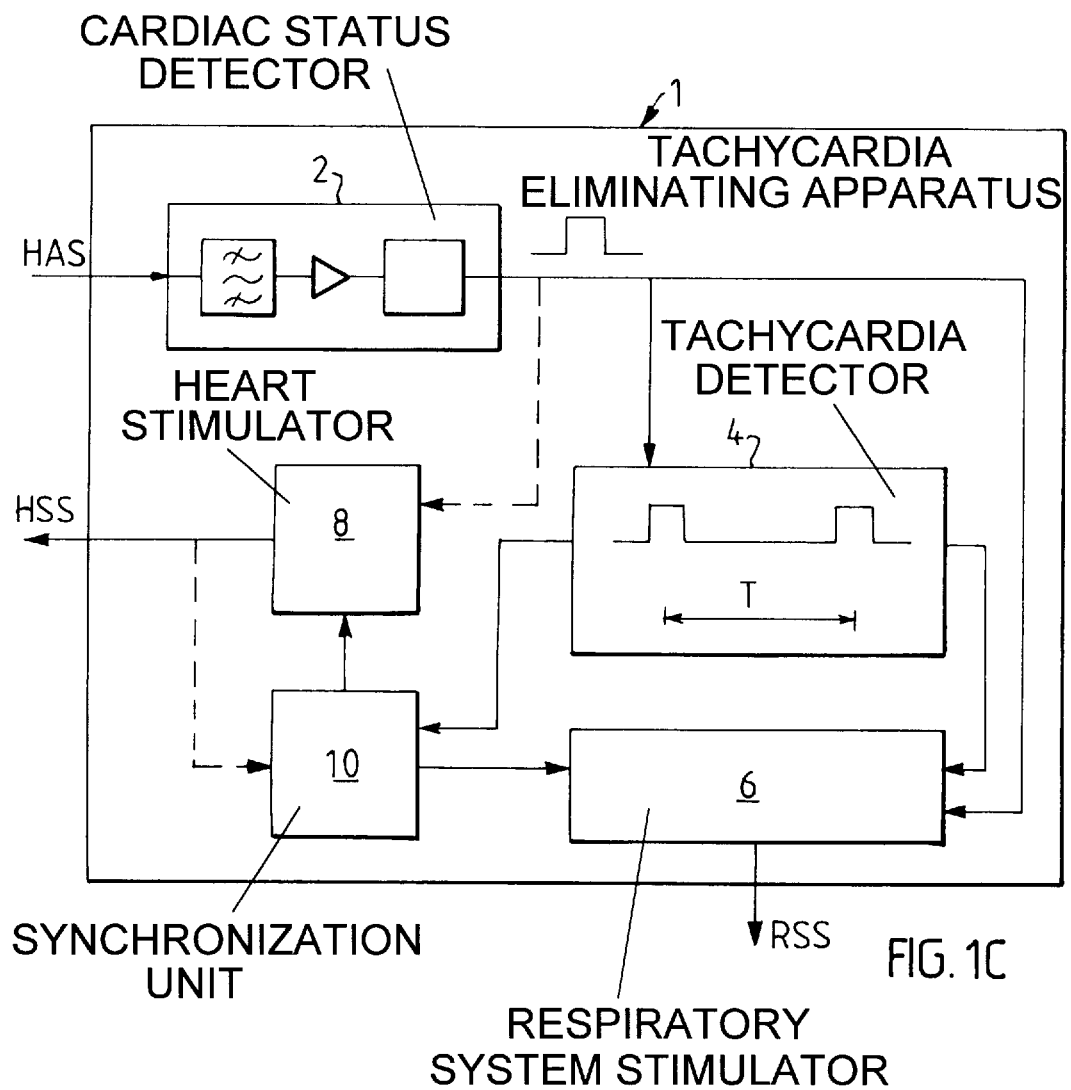
FIG. 1C shows another embodiment of the invention according to FIG. 1B.

FIG. 1A shows schematically an embodiment of an apparatus 1 for eliminating a tachycardia according to the present invention. Apparatuses of this kind are normally realized with logic circuits, but may also be designed in more traditional circuitry. FIG. 1A depicts functional features of the invention by means of block diagrams.

In FIG. 1A, a tachycardia eliminating apparatus 1 is coupled to a human body 7 and obtains, via a detection lead 3, an input cardiac activity signal HAS that represents the activity of the heart 9. Different cardiac activity signals reflecting, for example, heartbeats, blood pressure, blood flow, measured impedance or chemical composition of the blood are possible within the inventive concept.

The cardiac activity signal HAS is supplied to in a cardiac status detector 2 which is devised to detect the status of the cardiac system and to deliver an output cardiac status signal. An output of the cardiac status detector 2 is coupled to an input of a tachycardia detector 4, which is devised to detect, in the cardiac status signal, indications of an approaching or an established tachycardia and to deliver an output tachycardia indication signal in response to a deviation from a predetermined cardiac status. An output of the tachycardia detector is coupled to an input of a respiratory system stimulator 6, to which a tachycardia indicating signal is delivered. The respiratory system stimulator 6 is devised to generate, in response to a received tachycardia indication signal, an output respiratory system stimulation signal RSS suitable for stimulating a respiratory system organ to achieve a breathing rate corresponding to a predetermined desired heartbeat rate. In FIG. 1A the respiratory stimulating signal RS S is delivered by means of a respiratory system stimulation lead 5 to the diaphragm 22.

In the embodiment of the invention as shown in FIG. 1A, a heart activity signal HAS is obtained from the heart 9 and is delivered to a heartbeat detector 2 for detecting heartbeats in a known manner. The heart activity signal HAS is, for example, an ECG signal sensed by means of a surface electrode or an implantable sensing electrode. The heartbeat detector 2 is devised to deliver an output heartbeat signal indicating each detected heartbeat, e.g. in the form of a square wave signal were each positive edge indicates a heartbeat. The tachycardia detector 4 is coupled to the output of the heartbeat detector 2 add is devised to detect a tachycardia and/or single ectopic beats of the heart as reflected in the heartbeat signal. For this purpose the tachycardia detector 4 may, for example, be devised to compare the detected heartbeat rate with a predetermined limit value, e.g. 150 beats/minute, and detect whether the limit value is exceeded. The tachycardia detector 4 is further devised to generate and deliver an output tachycardia indication signal in response to a detected tachycardia status of the heart via the heartbeat signal. An output of the tachycardia detector 4 is coupled to an input of the respiratory system stimulator 6. The respiratory system stimulator 6 is devised to generate an output respiratory system stimulation signal RSS in response to a tachycardia indication signal. The respiratory system stimulation signal RSS may have different forms but must be suitable for stimulating a selected organ of a patient's respiratory system in order to achieve a certain breathing rate, with, for example the ratio of the detected heartbeat rate to the stimulated breathing rate corresponding to a predetermined value.

The respiratory system stimulator 6 is, in one embodiment of the invention, devised to generate a respiratory system stimulation signal RSS such that the quotient of the detected heartbeat rate divided by the stimulated breathing rate is a positive integer (1,2,3 . . . ) within reasonable values. In another embodiment the respiratory system stimulator 6 is devised to generate an output respiratory system stimulation signal (RSS) suitable for stimulating a respiratory system to a breathing rate close to a predetermined desired heartbeat rate, with a possible deviation in the breathing rate from the predetermined desired heartbeat rate up to about ⅓ to about ½ of the value of said desired heartbeat rate. The breathing may thus be stimulated to a breathing rate e.g. in the range: desired heartbeat rate x (I–½) to desired heartbeat rate x (I+½); or in a more narrow range.

FIG. 1B, which uses the same reference numerals as FIG. 1A for common components, shows an embodiment of the invention including a heart stimulator 8 for direct electrical stimulation of the heart in parallel with respiratory system stimulation. An input of the heart stimulator 8 is coupled to an output of the tachycardia detector 4 in order to obtain a tachycardia indication signal. The heart stimulator 8 includes a known pulse generator (not shown) and is devised to generate an output heart stimulation signal HSS suitable for direct heart stimulation via a heart stimulating electrode. As shown in FIG. 1B with a dashed line, the heart stimulator 8 may optionally also be coupled to the output of the heartbeat detector 2 in order to obtain a heartbeat signal. The heart stimulator 8 of this embodiment is devised to generate a heart stimulation signal in a known pacing or defibrillating manner, in parallel with or fully independently of generating a heart stimulation signal in response to a tachycardia indication signal.

FIG. 1C shows a further embodiment of the invention according to FIG. 1B provided in order to achieve a more finely tuned direct and indirect heart stimulation. For this purpose the tachycardia eliminating apparatus includes a synchronization unit 10 for synchronizing the respiratory system stimulation signal RSS with the direct heart stimulation signal HSS. An input of the synchronization means 10 is coupled to an output of the tachycardia detector 4, whereas trigger signal outputs of the synchronization unit 10 are coupled to inputs of the heart stimulator 8 and the respiratory system stimulator 6, respectively. Functionally, the synchronization unit 10 is devised to trigger the heart stimulator 8 and the respiratory system stimulator 6 to deliver respective stimulation signals HSS and RSS in response to a tachycardia indication signal. The respiratory system stimulator 6 and the heart stimulator are naturally correspondingly devised to be triggered by trigger signals. The synchronization is carried out such that the respiratory system stimulation signal RSS has a predetermined time relation to the heart stimulation signal HSS. In a further version of this embodiment there may also be an optional feed-back coupling from an output of the heart stimulator 8 to an input of the synchronization unit 10, in order to enable a refinement of the synchronization in response to a feed-back heart stimulation signal HSS. In a further embodiment as depicted in FIG. 1C, an input of the heart stimulator 8 may be optionally coupled to the output of the heartbeat detector in order to generate and deliver a heart stimulation signal in a known manner.

Figure 2:
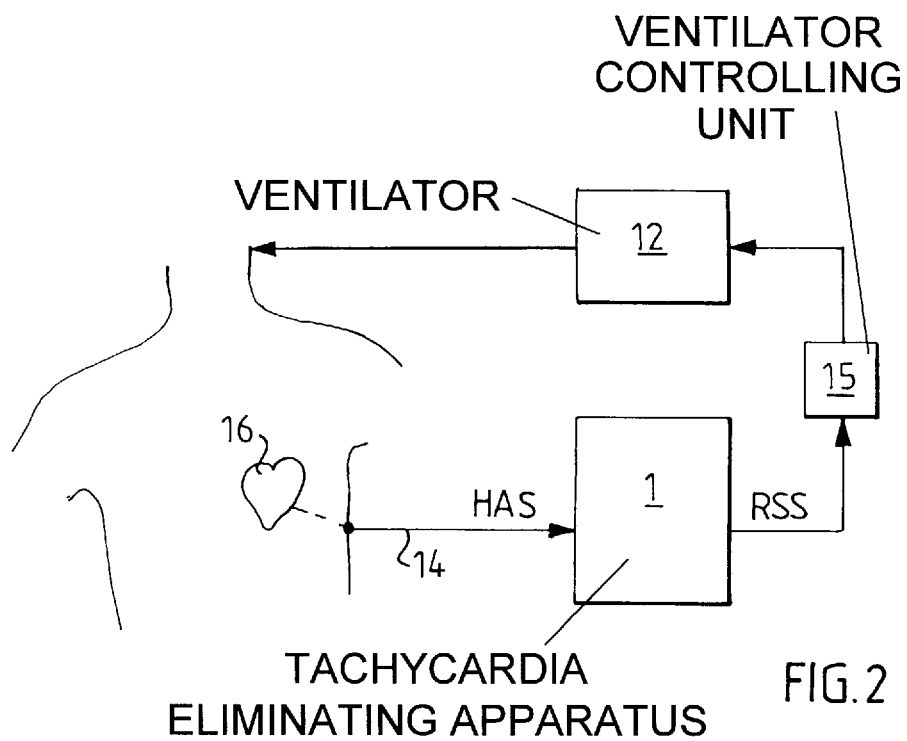
FIG. 2 shows an embodiment of the invention suitable for use together with a ventilator.

FIG. 2 schematically shows an inventive apparatus I in an embodiment devised for external use. The apparatus I receives a heart activity signal HAS from a heart 16 via an electrode lead 14. A generated respiratory system stimulation signal RSS suitable for controlling a ventilator is delivered to a ventilator controlling unit 15, which is coupled to an output of the apparatus I and to an input of a ventilator 12. The ventilator controlling unit 15 is devised to control the ventilator 12 in response to a respiratory system stimulating signal RSS delivered by the apparatus 1.

Figure 3:
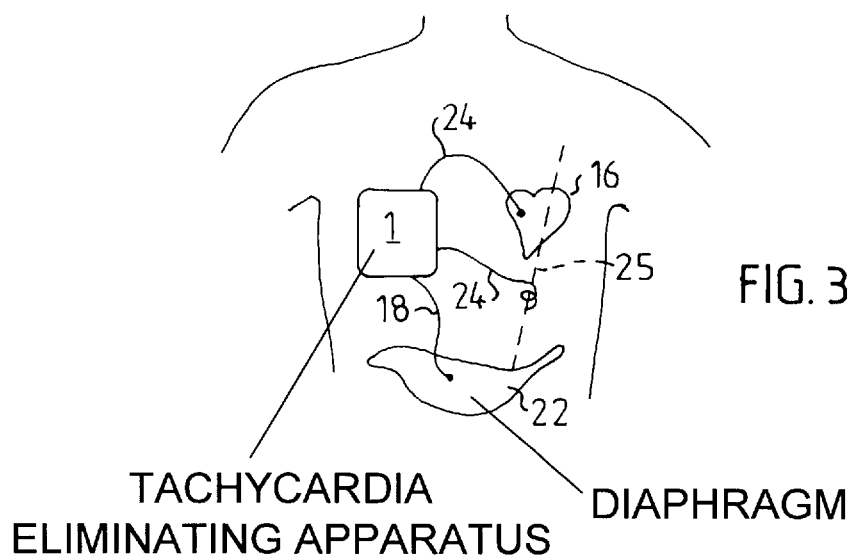
FIG. 3 shows an implantable embodiment of the invention devised for stimulating a respiratory system muscle or a respiratory system nerve and possibly also for stimulating the heart.

FIG. 3 shows an implantable tachycardia eliminating apparatus I according to the invention and schematically depicted when implanted in a patient's body. The apparatus 1 is coupled to a sensing (and possibly also stimulating) electrode 24 which, at its distal end, is coupled to heart tissue. The apparatus I of the shown embodiment is also coupled to nervus pherenicus 25 via a nerve stimulation lead 24 and to the diaphragm 22 via a muscle stimulation lead 18. This configuration of a system to stimulate the respiratory system is merely shown as an example, and other muscles or nerves of the respiratory system may be stimulated together or separately. In the embodiment for stimulating a respiratory muscle, the respiratory system stimulator of the tachycardia eliminating apparatus 1 is devised to deliver a stimulation signal RSS suitable for stimulating the selected respiratory system muscle. Similarly, in the embodiment for stimulating a nerve, the respiratory system stimulator 6 is devised to deliver a stimulation signal RSS suitable for stimulating a selected respiratory system nerve.

The form of the signals needed in the different cases depends on the anatomic qualities of the specific, selected organ. Examples of signals involved with and generated by the inventive apparatus are shown in diagrams in FIGS. 4–7. In FIG. 4 the signal S1 is a typical ECG signal plotted as a voltage U over a time scale t. FIG. 5 represents respiration signals S2, S3 with air pressure P plotted over the same time scale t as in FIG. 4. Signal S2 depicts a normal breathing rate, whereas signal S3 shows an accelerated breathing rate stimulated by means of an apparatus according to the invention.

FIG. 6 shows an example of a stimulation signal S4 for stimulation of respiratory muscles or nerves with a voltage plotted again over the common time scale t. Stimulation of respiratory muscles and nerves in order to achieve a contraction phase is preferably effected by means of a pulse train with a duration T1 of e.g. 2–5 milliseconds. Such pulse trains may be repeatedly delivered with a frequency for example in the range 5–100 Hz, i.e. a pulse train period T2 of 0.01–0.2 seconds. Stimulation pulses with this kind of pulse trains are produced for a period T3 which may have a predetermined length in order to achieve a desired heart rhythm, or for a period T3 that is continuously determined in response to a sensed heart activity signal.

The stimulation pulses may be positive, negative or biphasic. FIG. 7 shows such a biphasic pulse with an amplitude U, pulse width T4 and pulse period T5. The values as well as the timing of the different signal parameters are selected with respect to the specifically selected organ of the respiratory system that is to be stimulated. However, examples of typical values would for the amplitude U be I–12 volts, for the pulse width 0.1–2 milliseconds and for the pulse period T5 about 10–200 milliseconds. In the embodiment of an external apparatus controlling a ventilator the respiratory system stimulation signal is not a pulse train but rather a signal suitable for controlling ventilator beats.

While preferred embodiments of the invention have been disclosed in detail, it should be understood by those skilled in the art that various other modifications may be made to the illustrated embodiments without departing from the scope of the invention as described in the specification and defined in the appended claims.

We claim as our invention:

1. A tachycardia eliminating apparatus comprising:
   means for obtaining a cardiac activity signal from a patient;
   cardiac status detecting means, supplied with said cardiac activity signal, for detecting a status of a cardiac system and for generating an output cardiac status signal;
   tachycardia detecting means, supplied with said output cardiac status signal, for identifying at least one of impending tachycardia and established tachycardia and for generating an output tachycardia indication signal dependent on a deviation of said output cardiac status signal from a predetermined cardiac status; and
   respiratory system stimulating means, supplied with said output tachycardia indication signal, for generating, in response to an indication of impending or established tachycardia, an output respiratory system stimulation signal for stimulating a respiratory system organ for producing a breathing rate corresponding to a predetermined heartbeat rate.

2. The tachycardia eliminating apparatus as claimed in claim I wherein said means for obtaining a cardiac activity signal comprises means for obtaining a heartbeat signal, and wherein said cardiac status detecting means comprises a heartbeat detector.

3. The tachycardia eliminating apparatus as claimed in claim 2 wherein said tachycardia detecting means comprises means for generating said output tachycardia indication signal if a heartbeat rate, detected by said heartbeat detector, exceeds a predetermined limit value.

4. The tachycardia eliminating apparatus as claimed in claim 2 wherein said respiratory system stimulating means comprises means for generating a respiratory system stimulation signal for producing a breathing rate such that a quotient of said heartbeat rate detected by said heartbeat detector divided by said breathing rate is a positive integer.

5. The tachycardia eliminating apparatus as claimed in claim 1 wherein said respiratory system stimulating means comprises means for producing a breathing rate deviating from said predetermined heartbeat rate in a range between about one-third to about one-half of said predetermined heartbeat rate.

6. The tachycardia eliminating apparatus as claimed in claim 1 wherein said respiratory system stimulating means comprises means adapted for stimulating a respiratory system muscle.

7. The tachycardia eliminating apparatus as claimed in claim 6 wherein said respiratory stimulating means comprises means adapted for stimulating a diaphragm.

8. The tachycardia eliminating apparatus as claimed in claim 1 wherein said respiratory system stimulating means comprises means adapted for stimulating a respiratory system nerve.

9. The tachycardia eliminating apparatus as claimed in claim 8 wherein said respiratory system stimulating means comprises means for stimulating a nervus pherenicus.

10. The tachycardia eliminating apparatus as claimed in claim I further comprising a ventilator, said ventilator comprising ventilator control means, supplied with said output respiratory system stimulation signal, for controlling said ventilator for producing respiration in a patient at said breathing rate corresponding to said predetermined heartbeat rate.

11. The tachycardia eliminating apparatus as claimed in claim 1 further comprising heart stimulating means, supplied with said output tachycardia indication signal, for directly stimulating a heart in response to said tachycardia indication signal.

12. The tachycardia eliminating apparatus as claimed in claim 11 further comprising synchronization means, supplied with said output tachycardia indication signal, for respectively triggering said heart stimulating means and said respiratory system stimulating means for giving said respiratory system stimulation signal a predetermined chronological relation to said heart stimulation signal.

13. The tachycardia eliminating apparatus as claimed in claim 12 wherein said synchronization means includes a feedback path for feeding back said heart stimulating signal to said synchronization means.

14. The tachycardia eliminating apparatus as claimed in claim 1 wherein said means for obtaining a cardiac activity signal comprises an implantable electrode, and further comprising a housing, adapted for implantation in a patient, containing said cardiac status detecting means, said tachycardia detecting means, and said respiratory system stimulating means.

* * * * *